US010339937B2

(12) United States Patent
Koll et al.

(10) Patent No.: US 10,339,937 B2
(45) Date of Patent: *Jul. 2, 2019

(54) AUTOMATIC DECISION SUPPORT

(71) Applicant: MModal IP LLC, Franklin, TN (US)

(72) Inventors: Detlef Koll, Pittsburgh, PA (US); Michael Finke, Pittsburgh, PA (US)

(73) Assignee: MModal IP LLC, Franklin, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/892,876

(22) Filed: Feb. 9, 2018

(65) Prior Publication Data

US 2018/0166081 A1    Jun. 14, 2018

Related U.S. Application Data

(63) Continuation of application No. 13/888,290, filed on May 6, 2013, now Pat. No. 9,892,734, which is a
(Continued)

(51) Int. Cl.
G06F 17/21 (2006.01)
G06F 17/27 (2006.01)
(Continued)

(52) U.S. Cl.
CPC ............ *G10L 19/00* (2013.01); *G06F 17/211* (2013.01); *G06F 17/2785* (2013.01);
(Continued)

(58) Field of Classification Search
CPC ......... G10L 19/00; G10L 15/02; G10L 15/26; G10L 704/257; G16H 10/60; G16H 15/00;
(Continued)

(56) References Cited

U.S. PATENT DOCUMENTS 7,475,019 B2 * 1/2009 Rosenfeld ............. G06F 19/325
705/2
8,756,234 B1 * 6/2014 Dreyer ................... G06F 19/00
707/739
(Continued)

FOREIGN PATENT DOCUMENTS

CA     2813608 C    4/2012
EP     2030198 B1   8/2018

OTHER PUBLICATIONS

Communication pursuant to Art 94(3) EPC dated Jan. 3, 2019 in European Patent application No. 07 784 507.1.
(Continued)

*Primary Examiner* — Fariba Sirjani
(74) *Attorney, Agent, or Firm* — Blueshift IP, LLC; Robert Plotkin

(57) ABSTRACT

Speech is transcribed to produce a transcript. At least some of the text in the transcript is encoded as data. These codings may be verified for accuracy and corrected if inaccurate. The resulting transcript is provided to a decision support system to perform functions such as checking for drug-drug, drug-allergy, and drug-procedure interactions, and checking against clinical performance measures (such as recommended treatments). Alerts and other information output by the decision support system are associated with the transcript. The transcript and associated decision support output are provided to a physician to assist the physician in reviewing the transcript and in taking any appropriate action in response to the transcript.

10 Claims, 2 Drawing Sheets

Related U.S. Application Data continuation of application No. 11/766,780, filed on Jun. 21, 2007, now abandoned.

(60) Provisional application No. 60/815,689, filed on Jun. 22, 2006, provisional application No. 60/815,688, filed on Jun. 22, 2006, provisional application No. 60/815,687, filed on Jun. 22, 2006.

(51) Int. Cl.

| | | |
|---|---|---|
| *G06Q 50/22* | (2018.01) | |
| *G06Q 50/24* | (2012.01) | |
| *G10L 15/02* | (2006.01) | |
| *G10L 15/26* | (2006.01) | |
| *G10L 19/00* | (2013.01) | |
| *G16H 10/20* | (2018.01) | |
| *G16H 10/60* | (2018.01) | |
| *G16H 15/00* | (2018.01) | |
| *G06F 19/00* | (2018.01) | |

(52) U.S. Cl.
CPC ............. *G06F 19/00* (2013.01); *G06Q 50/22* (2013.01); *G06Q 50/24* (2013.01); *G10L 15/02* (2013.01); *G10L 15/26* (2013.01); *G16H 10/20* (2018.01); *G16H 10/60* (2018.01); *G16H 15/00* (2018.01)

(58) Field of Classification Search
CPC ... G16H 10/20; G06F 17/211; G06F 17/2785; G06F 19/00; G06Q 50/22; G06Q 50/24
See application file for complete search history.

(56) References Cited

U.S. PATENT DOCUMENTS

| | | | | |
|---|---|---|---|---|
| 9,892,734 | B2* | 2/2018 | Koll | ....................... G06F 17/211 |
| 2003/0069759 | A1* | 4/2003 | Smith | ................... G06F 19/328 |
| | | | | 705/3 |
| 2003/0163348 | A1* | 8/2003 | Stead | ..................... G16H 40/20 |
| | | | | 705/2 |

OTHER PUBLICATIONS

Friedman, C. and Hripcsak, G., "Natural language processing and its future in medicine," Academic Medicine, vol. 74, No. 8, pp. 890-895, (Aug. 1999).

Bates, D.W. et al., "Detecting Adverse Events Using Information Technology," Journal of the American Medical Informatics Association, vol. 10, No. 2, pp. 115-128, (Mar. 1, 2003).

Ginneken, "The computerized patient record: balancing effort and benefit", International Journal of Medical Informatics, vol. 65, No. 2, pp. 97-119, (Jun. 1, 2002).

Tang, P. C. et al., "Semantic integration of information in a physician's workstation," International Journal of Bio-Medical Computing, vol. 35, No. 1, pp. 47-60, (Feb. 1, 1994).

Examiner's Report dated Jan. 16, 2019, in Canadian patent application No. 2,652,444.

Communication pursuant to Art 94(3) EPC dated Oct. 1, 2018 in European Patent application No. 07 784 507.1.

* cited by examiner

AUTOMATIC DECISION SUPPORT

CROSS REFERENCE TO RELATED APPLICATIONS

This application is related to the commonly-owned U.S. patent application Ser. No. 10/923,517, filed on Aug. 20, 2004, entitled "Automated Extraction of Semantic Content and Generation of a Structured Document from Speech," which is hereby incorporated by reference herein.

BACKGROUND

It is desirable in many contexts to generate a structured textual document based on human speech. In the legal profession, for example, transcriptionists transcribe testimony given in court proceedings and in depositions to produce a written transcript of the testimony. Similarly, in the medical profession, transcripts are produced of diagnoses, prognoses, prescriptions, and other information dictated by doctors and other medical professionals.

Producing such transcripts can be time-consuming. For example, the speed with which a human transcriptionist can produce a transcript is limited by the transcriptionist's typing speed and ability to understand the speech being transcribed. Although software-based automatic speech recognizers are often used to supplement or replace the role of the human transcriptionist in producing an initial transcript, even a transcript produced by a combination of human transcriptionist and automatic speech recognizer will contain errors. Any transcript that is produced, therefore, must be considered to be a draft, to which some form of error correction is to be applied.

Producing a transcript is time-consuming for these and other reasons. For example, it may be desirable or necessary for certain kinds of transcripts (such as medical reports) to be stored and/or displayed in a particular format. Providing a transcript in an appropriate format typically requires some combination of human editing and automatic processing, which introduces an additional delay into the production of the final transcript.

Consumers of reports, such as doctors and radiologists in the medical context, often stand to benefit from receiving reports quickly. If a diagnosis depends on the availability of a certain report, for example, then the diagnosis cannot be provided until the required report is ready. For these and other reasons it is desirable to increase the speed with which transcripts and other kinds of reports derived from speech may be produced, without sacrificing accuracy.

Furthermore, even when a report is provided quickly to its consumer, the consumer typically must read and interpret the report in order to decide on which action, if any, to take in response to the report. Performing such interpretation and making such decisions may be time-consuming and require significant training and skill. In the medical context, for example, it would be desirable to facilitate the process of acting on reports, particularly in time-critical situations.

SUMMARY

Speech is transcribed to produce a transcript. At least some of the text in the transcript is encoded as data. These codings may be verified for accuracy and corrected if inaccurate. The resulting transcript is provided to a decision support system to perform functions such as checking for drug-drug, drug-allergy, and drug-procedure interactions, and checking against clinical performance measures (such as recommended treatments). Alerts and other information output by the decision support system are associated with the transcript. The transcript and associated decision support output are provided to a physician to assist the physician in reviewing the transcript and in taking any appropriate action in response to the transcript.

For example, one embodiment of the present invention is a computer-implemented method comprising: (A) applying an automatic speech recognizer to a spoken audio stream to produce a first document including first codings associated with text in the first document; (B) providing the first document to an automatic decision support system; (C) receiving, from the automatic decision support system, decision support output derived from the first document; and (D) transmitting to a recipient a second document, derived from the first document and the decision support output, wherein the second document does not include the first codings.

Another embodiment of the present invention is an apparatus comprising: speech recognition means for applying an automatic speech recognizer to a spoken audio stream to produce a first document including first codings associated with text in the first document; document provision means for providing the first document to an automatic decision support system; output receiving means for receiving, from the automatic decision support system, decision support output derived from the first document; and document transmission means for transmitting to a recipient a second document, derived from the first document and the decision support output, wherein the second document does not include the first codings.

Another embodiment of the present invention is a computer-implemented method comprising: (A) applying an automatic speech recognizer to a spoken audio stream to produce a first document including first codings associated with text in the first document; (B) applying a decision support method to the first document to produce decision support output; (C) storing a record associating the decision support output with the first document; and (D) transmitting to a recipient a second document, derived from the first document and the decision support output, wherein the second document does not include the first codings.

Another embodiment of the present invention is an apparatus comprising: speech recognition means for applying an automatic speech recognizer to a spoken audio stream to produce a first document including first codings associated with text in the first document; decision support means for applying a decision support method to the first document to produce decision support output; record storage means for storing a record associating the decision support output with the first document; and document transmission means for transmitting to a recipient a second document, derived from the first document and the decision support output, wherein the second document does not include the first codings.

Another embodiment of the present invention is a computer-implemented method comprising: (A) receiving, from a remote location, a spoken audio stream; (B) applying an automatic speech recognizer to the spoken audio stream to produce a first document including first codings associated with text in the first document; (C) providing the first document to an automatic decision support system; (D) receiving, from the automatic decision support system, decision support output derived from the first document; and (E) transmitting, to a recipient, at the remote location, a second document, derived from the first document and the decision support output.

Another embodiment of the present invention is an apparatus comprising: means for receiving, from a remote location, a spoken audio stream; means for applying an automatic speech recognizer to the spoken audio stream to produce a first document including first codings associated with text in the first document; means for providing the first document to an automatic decision support system; means for receiving, from the automatic decision support system, decision support output derived from the first document; and means for transmitting, to a recipient, at the remote location, a second document, derived from the first document and the decision support output.

Another embodiment of the present invention is a computer-implemented method comprising: (A) receiving a first portion of a streamed spoken audio stream from an audio stream transmitter; (B) applying an automatic speech recognizer to the stream spoken audio stream to produce a first partial document including first codings associated with text in the first partial document; (C) providing the first partial document to an automatic decision support system; (D) receiving, from the automatic decision support system, decision support output derived from the first partial document; (E) determining whether the decision support output satisfies a predetermined criterion triggering human review; (F) if the decision support output is determined to satisfy the predetermined criterion, then transmitting to the audio stream transmitter, while receiving a second portion of the streamed spoken audio stream, an indication that the decision support output satisfies the predetermined criterion.

Another embodiment of the present invention is an apparatus comprising: means for receiving a first portion of a streamed spoken audio stream from an audio stream transmitter; means for applying an automatic speech recognizer to the stream spoken audio stream to produce a first partial document including first codings associated with text in the first partial document; means for providing the first partial document to an automatic decision support system; means for receiving, from the automatic decision support system, decision support output derived from the first partial document; means for determining whether the decision support output satisfies a predetermined criterion triggering human review; and means for transmitting to the audio stream transmitter, while receiving a second portion of the streamed spoken audio stream, an indication that the decision support output satisfies the predetermined criterion if the decision support output is determined to satisfy the predetermined criterion.

Other features and advantages of various aspects and embodiments of the present invention will become apparent from the following description and from the claims.

DETAILED DESCRIPTION

Embodiments of the invention are directed to techniques for providing a transcript to a clinical decision support system for the purpose of attaching critical alerts and other information to the transcript for review by a physician. In general, speech is transcribed to produce a report. At least some of the text in the transcript is encoded as data. The codings may be verified for accuracy and corrected if inaccurate. The resulting transcript is provided to a decision support system to perform functions such as checking for drug-drug, drug-allergy, and drug-procedure interactions, and checking against clinical performance measures (such as recommended treatments). Alerts and other information provided by the decision support system are associated with the transcript. The transcript and associated decision support output are provided to a physician for review and any other appropriate action in response to the decision support output.

Figure 1:
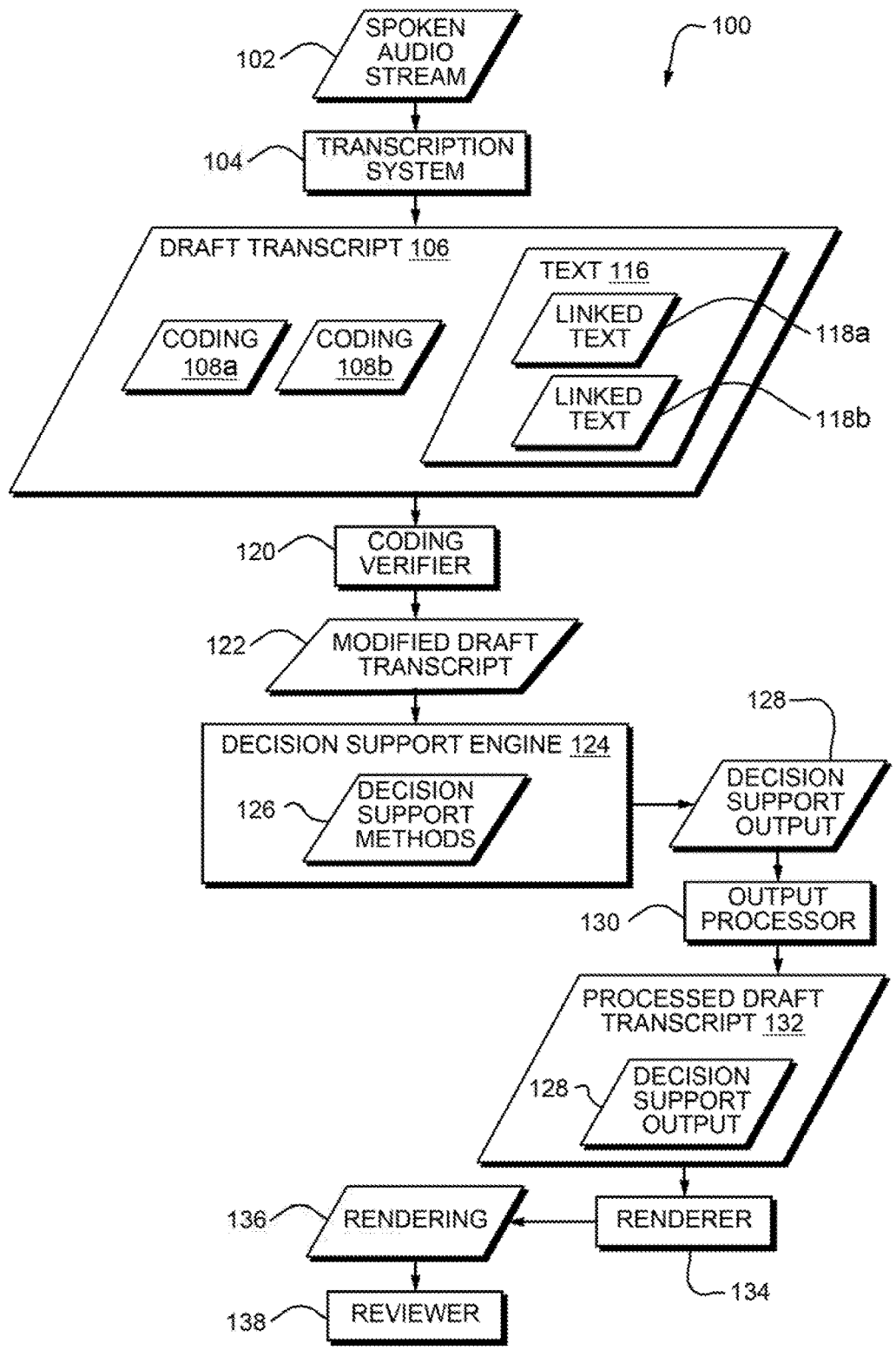
FIG. 1 is a dataflow diagram of a system for applying automatic clinical decision support to a transcript of speech.
Figure 2:
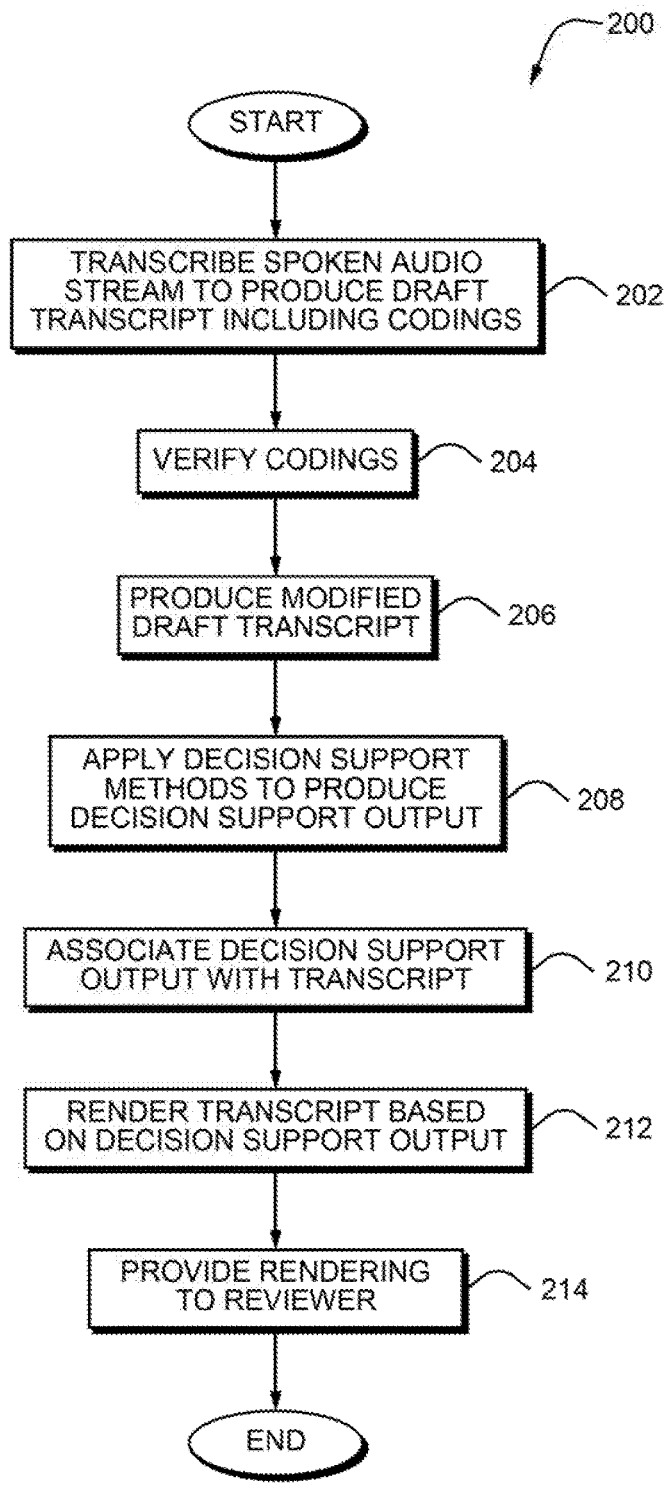
FIG. 2 is a flowchart of a method performed by the system of FIG. 1 according to one embodiment of the present invention.

More specifically, referring to FIG. 1, a dataflow diagram is shown of a system 100 for applying automatic clinical decision support to a transcript of speech. Referring to FIG. 2, a flowchart is shown of a method 200 performed by the system 100 of FIG. 1 according to one embodiment of the present invention.

A transcription system 104 transcribes a spoken audio stream 102 to produce a draft transcript 106 (step 202). The spoken audio stream 102 may, for example, be dictation by a doctor describing a patient visit. The spoken audio stream 102 may take any form. For example, it may be a live audio stream received directly or indirectly (such as over a telephone or IP connection), or an audio stream recorded on any medium and in any format.

The transcription system 104 may produce the draft transcript 106 using, for example, an automated speech recognizer or a combination of an automated speech recognizer and human transcriptionist. The transcription system 104 may, for example, produce the draft transcript 106 using any of the techniques disclosed in the above-referenced patent application entitled "Automated Extraction of Semantic Content and Generation of a Structured Document from Speech." As described therein, the draft transcript 106 may include text 116 that is either a literal (verbatim) transcript or a non-literal transcript of the spoken audio stream 102. As further described therein, although the draft transcript 106 may be a plain text document, the draft transcript 106 may also, for example, in whole or in part be a structured document, such as an XML document which delineates document sections and other kinds of document structure. Various standards exist for encoding structured documents, and for annotating parts of the structured text with discrete facts (data) that are in some way related to the structured text. Examples of existing techniques for encoding medical documents include the HL7 CDA v2 XML standard (ANSI-approved since May 2005), SNOMED CT, LOINC, CPT, ICD-9 and ICD-10, and UMLS.

As shown in FIG. 1, the draft transcript 106 includes one or more codings 108, each of which encodes a "concept" extracted from the spoken audio stream 102. The term "concept" is used herein as defined in the above-referenced patent application entitled "Automated Extraction of Semantic content and Generation of a Structured Document from Speech." Reference numeral 108 is used herein to refer generally to all of the codings within the draft transcript 106. Although in FIG. 1 only two codings, designated 108a and 108b, are shown, the draft transcript 106 may include any number of codings.

In the context of a medical report, each of the codings 108 may, for example, encode an allergy, prescription, diagnosis, or prognosis. In general, each of the codings 108 includes a code and corresponding data, which are not shown in FIG. 1 for ease of illustration. Each of the codings 108 may be linked to text in the transcript 106. For example, coding 108a may be linked to text 118a and coding 108b may be linked to text 118*b*. Further details of embodiments of the codings 108 may be found in the above-referenced patent application entitled, "Verification of Extracted Facts."

A coding verifier 120 may verify the codings 108 (step 204). Any of a variety of techniques may be used to verify the codings, examples of which may be found in the above-referenced patent application entitled, "Verification of Extracted Facts." The verification process performed by the coding verifier 120 may include correcting any codings that are found to be incorrect. The coding verifier 120 therefore produces a modified draft transcript 122, which includes any corrections to the codings 108 or other modifications made by the coding verifier 120 (step 206). Note, however, that it is optional to verify the codings 108.

The modified draft transcript 122 is provided to a decision support engine 124, which applies decision support methods 126 to the modified draft transcript 122 to produce decision support output 128 (step 208). If the codings 108 were not verified (e.g., if step 204 was not performed), then the original draft transcript 106, instead of the modified draft transcript 122, may be provided to the decision support engine 124 in step 208 to produce the decision support output 128. In other words, the draft transcript 106 may be unverified when decision support is applied to it.

An example of a decision support method is a method which checks for drug-drug, drug-allergy, and/or drug-procedure interactions. The decision support engine 124 may easily perform such a method because concepts such as drugs, allergies, and procedures have already been encoded in the modified draft transcript 122 in a form that is computer-readable. Therefore, the decision support engine 124 may use a database of drug-drug interactions, for example, to determine whether the modified draft transcript 122 describes any such interactions requiring attention of a physician.

Another example of a decision support method is a method which checks concepts encoded in the modified draft transcript 122 against clinical performance measures (such as recommended treatments). For example, the American Heart Association (AHA) recommends that patients who have had a heart attack, unstable angina, or ischemic stroke take aspirin regularly. Therefore, one of the decision support methods 126 may determine whether the draft transcript 106 (or modified draft transcript 122) indicates that the dictating physician stated that the patient has experienced a heart attack, unstable angina, or ischemic stroke. If so, the decision support method may further determine whether the draft transcript 106 (or modified draft transcript 122) recommends (e.g., in the "recommended treatments" section) that the patient take aspirin. If the decision support method determines that the patient has had one of the three indicated conditions and that the doctor did not recommend aspirin for the patient, then the decision support method may alert the physician (through the decision support output 128) to this fact and suggest that the physician recommend aspirin to the patient. Again, the decision support engine 124 may easily perform such a method because concepts such as the patient's medical history and recommended treatments have already been encoded in the transcripts 106 and 122 in a form that is computer-readable.

As stated above, the decision support engine 124 produces decision support output 128. An example of such output is a critical alert indicating that the transcript 122 states that the patient has been prescribed two drugs which are contraindicated with each other. The decision support engine 124 may be configured to label different components of the output 128 with different priority levels. For example, the decision support engine 124 may label certain components of the output 128 as requiring immediate physician review, while labeling other components of the output 128 as requiring physician review, but not immediately. Alternatively, for example, the decision support engine 124 may filter the results it produces and include in the output 128 only those pieces of information which exceed a certain priority level (e.g., only those pieces of information requiring immediate physician review).

A decision support output processor 130 may attach the decision support output 128 to the modified draft transcript 122 or otherwise associate the decision support output 128 with the modified draft transcript 122 (step 210). For example, in the embodiment shown in FIG. 1, the decision support output processor 130 stores the decision support output 128 within the modified draft transcript 122, thereby producing a processed draft transcript 132 containing the contents of both the modified draft transcript 122 and the decision support output 128.

As another example, decision support output processor 130 may use the decision support output 128 to modify the modified draft transcript 122. For example, if the decision support output 128 indicates a drug-drug allergy, the decision support output processor 130 may modify the code(s) for the contraindicated drug(s) in the transcript 122 so that the text corresponding to the drug(s) appears in boldface, in a conspicuous color (e.g., red), or in some other manner that calls attention to the text. As another example, the decision support output processor 130 may include in the transcript 122 a textual comment describing the drug-drug allergy such that the comment appears in the vicinity of the text when it is rendered.

The processed draft transcript 132 (and the decision support output 128, if it is not contained within the processed draft transcript 132) may be provided to a physician or other reviewer 138 for review. Alternatively, for example, information derived from the processed draft transcript 132 and/or decision support output 128 may be provided to the reviewer 138 for review. The reviewer 138 may be the same person as the dictator of the spoken audio stream 102.

For example, a renderer 134 may render the processed transcript 132 based on the decision support output 128 to produce a rendering 136 (step 212). The rendering 136 may display both the text of the transcript 132 and the output 128. As described above, the rendering 136 may reflect the output 128 in a variety of ways, such as by using the output 128 to modify the manner in which the text of the transcript 132 is rendered.

For example, the rendering 136 may be a flat text document or other document which does not include the codings 108*a-b* and other data which typically require an EMR and/or decision support system to process. For example, the rendering 136 may be a Rich Text Format (RTF) or HTML document suitable for display by a conventional word processor or web browser. The renderer 134 may, for example, strip out the codings 108*a-b* from the processed draft transcript 132 or otherwise process the draft transcript 132 to produce the rendering 136 in a format suitable for processing (e.g., displaying) without an on-site EMR and/or decision support system. The rendering 136, therefore, need not be directly or immediately displayed to the reviewer 138. For example, the renderer 134 may transmit the rendering 136 to the reviewer 138 electronically (e.g., by email, FTP, or HTTP), for subsequent viewing in any manner by the reviewer 138.

The reviewer 138 (e.g., physician) reviews the rendering 136. The system 100 may include an approval mechanism (not shown) which enables the reviewer 138 to provide input indicating whether the reviewer 138 approves of the transcript 132. In the medical context, for example, if the reviewer 138 is a physician, the physician may be required to sign off on the transcript 132, as represented by the rendering 136. The use of the decision support output 128 in the process of producing the rendering 136 facilitates the process of reviewing the transcript 132. For example, if the output 128 indicates that the transcript 122 describes a particular drug-drug allergy, then the rendering 136 may display a conspicuous indication of such allergy, thereby increasing the likelihood that the physician-reviewer 138 will notice such an allergy and decreasing the time required for the physician-reviewer 138 to do so.

Embodiments of the present invention have a variety of advantages. For example, in conventional systems, a physician typically dictates a report. The report is transcribed and the transcript is presented to the physician for review and signature. The physician must conclude that the report is accurate before signing it. If the physician's facility does not have an onsite EMR system and/or decision support system, then it may not be possible or feasible for decision support to be applied to the report before presenting it to the physician for signature. As a result, the physician must review and sign the report, thereby attesting to its accuracy, without the additional assurance of accuracy that a decision support system may provide.

In contrast, the techniques disclosed herein facilitate the process of applying decision support and other quality assurance measures to a draft report before providing the report to the physician for signature, i.e., while the report is still in its unsigned state. As a result, the techniques disclosed herein may be used both to increase the quality of signed reports and to reduce the amount of time required by physicians to review reports before signing.

In particular, the techniques disclosed herein may be used to bring the benefits of automatic clinical decision support and other automated quality assurance measures to care providers who do not have an on-site Electronic Medical Record (EMR) system which is capable of consuming coded document formats. Such EMR systems are costly and therefore are not used by small clinics. Embodiments of the present invention do not require an on-site EMR system because all processing of encoded documents may be integrated into the transcription workflow and therefore performed by, for example, an outsourced transcription service at a remote location in relation to the clinic or other source organization. The dictator of speech may, for example, transmit the spoken audio stream 102 to such a service at a remote location in any manner, such as by electronic transmission.

The service may then perform method 200 (FIG. 2) at an off-site location in relation to the dictator of speech 102. The service may then transmit the processed draft transcript 132, decision support output 128, and/or the rendering 136 to the reviewer 138 in any manner, such as by any form of electronic transmission. If the reviewer 138 does not have an on-site EMR and/or decision support system, however, the service may provide the transcript 132, decision support output 128, and/or rendering 136 to the reviewer 138 in a flat text format or other format that does not require the reviewer 138 to have an on-site EMR or decision support system to process. For example, the service may provide only the rendering 136, and not the processed draft transcript 132 or decision support output 128, to the reviewer 138. Therefore, embodiments of the present invention may be used to provide the benefits of automatic clinical decision support systems to providers through medical transcription services without requiring deployment of EMR systems on the provider side.

More generally, embodiments of the present invention use a human transcription workflow to enable automatic clinical decision support, disease management, and performance tracking. As described above, conventional transcription systems typically produce transcripts which are "flat" text documents, and which therefore are not suitable for acting as input to decision support processes. In contrast, embodiments of the present invention produce transcripts including structured data which encode concepts such as allergies and medications, and which therefore may be processed easily by automatic decision support systems. Such embodiments may therefore be integrated with clinical decision support systems and provide the benefits of such systems quickly and easily.

It is difficult or impossible to use flat text transcripts in this way because a decision support system would need first to interpret such text to apply decision support methods to it. Any attempt to use human intervention and/or natural language processing to perform such interpretation will suffer from the slow turnaround times and relatively high error rates associated with such techniques. In contrast, and as described in more detail in the above-referenced patent applications, transcripts may be produced using embodiments of the present invention quickly and with a high degree of accuracy, thereby making such transcripts particularly suitable for use as input to automatic clinical decision support systems.

Even in cases in which the system 100 of FIG. 1 is implemented in conjunction with an outsourced transcription service, the techniques disclosed herein do not require the entire spoken audio stream 102 to be spoken before clinical decision support may be applied to it. For example, consider a case in which a physician dictates the spoken audio stream 102 into a handheld recording device, which streams the spoken audio stream 102 to the transcription system 104 while the physician is speaking the spoken audio stream 102. The transcription system 104 may begin transcribing the beginning of the spoken audio stream 102 while the physician dictates subsequent portions of the spoken audio stream 102, which continue to be streamed to the transcription system 104. As the draft transcript 106 is being produced, it may be processed by the remainder of the system 100 as described above with respect to FIGS. 1 and 2.

As a result, if the decision support system 124 identifies a problem (such as a drug-drug allergy) requiring physician review, the decision support output 128 (e.g., in the form of the processed draft transcript 132 and/or the rendering 136) may be provided to the physician-reviewer 138 while the physician is still dictating the remainder of the spoken audio stream, i.e., before the entire spoken audio stream 102 has been transmitted to the transcription system 104 and before the entire draft transcript 106 has been produced. One benefit of such real-time application of decision support to the spoken audio stream 102 is that the decision support output 128 may be provided to the dictating physician before the physician has finished dictating, thereby presenting the physician with an opportunity to correct any errors during a single dictation session and while the correct content of the session is still fresh in the physician's mind.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Although certain examples provided herein involve documents generated by a speech recognizer, this is not a requirement of the present invention. Rather, the techniques disclosed herein may be applied to any kind of document, regardless of how it was generated. Such techniques may, for example, be used in conjunction with documents typed using conventional text editors.

The spoken audio stream 102 may be any audio stream, such as a live audio stream received directly or indirectly (such as over a telephone or IP connection), or an audio stream recorded on any medium and in any format. In distributed speech recognition (DSR), a client performs preprocessing on an audio stream to produce a processed audio stream that is transmitted to a server, which performs speech recognition on the processed audio stream. The audio stream may, for example, be a processed audio stream produced by a DSR client.

The invention is not limited to any of the described domains (such as the medical and legal fields), but generally applies to any kind of documents in any domain. For example, although the reviewer 138 may be described herein as a physician, this is not a limitation of the present invention. Rather, the reviewer 138 may be any person. Furthermore, documents used in conjunction with embodiments of the present invention may be represented in any machine-readable form. Such forms include plain text documents and structured documents represented in markup languages such as XML. Such documents may be stored in any computer-readable medium and transmitted using any kind of communications channel and protocol.

Furthermore, although particular examples are described herein in conjunction with clinical decision support, this is not a limitation of the present invention. Rather, the techniques disclosed herein may be applied to other forms of automated decision support based on transcripts containing structured text with encoded data. For example, the techniques disclosed herein may be used to verify document completeness, such as whether the dictator of the transcript 106 mistakenly omitted a required section of the transcript 106.

The decision support engine 124 may include any mechanism, such as a software- or hardware-based mechanism, for applying automatic decision support to the modified draft transcript 122. Although the decision support engine 124 may be described herein as applying automated methods, this does not preclude some degree of human interaction with the decision support engine 124 to perform its functions.

Furthermore, the decision support engine 124 may receive inputs in addition to the modified draft transcript 122 to assist in providing decision support. For example, a transcription service may produce multiple transcripts over time describing a single patient. In the course of producing such transcripts, the transcription service may build an archive of data about the patient, derived from data in the transcripts. Then, when the transcription service receives a new spoken audio stream for transcription, the transcription service may identify that the new spoken audio stream refers to a patient for whom a data archive already exists. The transcription service may then provide not only the current draft transcript, but also some or all of the patient's data archive, to the decision support engine 124. The decision support engine 124 may benefit from such additional data about the patient, such as medications previously prescribed to the patient, to detect drug-drug allergies or other problems which could not be detected from the current transcript in isolation.

The techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

The invention claimed is:

1. A computer-implemented method comprising:
   (A) applying an automatic speech recognizer to a spoken audio stream, from a physician or a medical professional describing a condition of a patient, to produce a first document including text, the first document being a transcript of a medical report;
   (B) extracting a plurality of concepts from the first document;
   (C) including a plurality of codings, representing the plurality of concepts, in the first document, wherein each of the plurality of codings represents one of an allergy, prescriptions, diagnosis, and prognosis, and wherein each of the plurality of codings is linked to a portion of the text in the first document;
(D) verifying accuracy of the codings in the first document to produce a verified document, wherein the verifying corrects any codings that are found to be incorrect;
(E) providing the verified document to an automatic decision support system, wherein the automatic decision support system:
determines whether the verified document provided to the automatic decision support system indicates satisfaction of a clinical performance measure and at least one of a drug-drug, drug-allergy, and drug-procedure interaction; and
filters the decision support output to include at least one component of the decision support output that has a filtered priority level that exceeds a predefined priority level;
(F) receiving, from the automatic decision support system, decision support output derived from the verified document, including the filtered priority level and an alert indicating that the verified document does not indicate satisfaction of the clinical performance measure and indicates at least one of a drug-drug, drug-allergy, and drug-procedure interaction;
(G) modifying verified document based on the decision support output, wherein the modifying of the verified document modifies the codings and adds textual comments to the verified document;
(H) rendering the modified verified document to display both the first document and the modified verified document in a rendered output;
(I) providing the rendered output to a reviewer, the reviewer including the physician or the medical professional or to another physician or medical professional; and
(J) receiving an approval of the transcript from the reviewer.

2. The method of claim 1, further comprising:
(K) storing a record associating the decision support output with the verified document.

3. The method of claim 1, further comprising:
(K) rendering the verified document based on the decision support output to produce a rendering of the verified document.

4. The method of claim 1, further comprising:
(K) before (F), at the automatic decision support system, determining that the verified document does not indicate satisfaction of the clinical performance measure.

5. The method of claim 4, wherein (K) further comprises, before (F), at the automatic decision support system, labeling a first component of the decision support output with a first priority level and labeling a second component of the decision support output with a second priority level that differs from the first priority level.

6. A non-transitory computer-readable medium comprising computer program instructions executable by a computer processor to execute a method, the method comprising:
(A) applying an automatic speech recognizer to a spoken audio stream, from a physician or a medical professional describing a condition of a patient, to produce a first document including text, the first document being a transcript of a medical report;
(B) extracting a plurality of concepts from the first document;
(C) including a plurality of codings, representing the plurality of concepts, in the first document, wherein each of the plurality of codings represents one of an allergy, prescriptions, diagnosis, and prognosis, and wherein each of the plurality of codings is linked to a portion of the text in the first document;
(D) verifying accuracy of the codings in the first document to produce a verified document, wherein the verifying corrects any codings that are found to be incorrect;
(E) providing the verified document to an automatic decision support system, wherein the automatic decision support system:
determines whether the verified document provided to the automatic decision support system indicates satisfaction of a clinical performance measure and at least one of a drug-drug, drug-allergy, and drug-procedure interaction; and
filters the decision support output to include at least one component of the decision support output that has a filtered priority level that exceeds a predefined priority level;
(F) receiving, from the automatic decision support system, decision support output derived from the verified document, including the filtered priority level and an alert indicating that the verified document does not indicate satisfaction of the clinical performance measure and indicates at least one of a drug-drug, drug-allergy, and drug-procedure interaction;
(G) modifying verified document based on the decision support output, wherein the modifying of the verified document modifies the codings and adds textual comments to the verified document;
(H) rendering the modified verified document to display both the first document and the modified verified document in a rendered output;
(I) providing the rendered output to a reviewer, the reviewer including the physician or the medical professional or to another physician or medical professional; and
(J) receiving an approval of the transcript from the reviewer.

7. The non-transitory computer-readable medium of claim 6, wherein the computer program instructions comprise instructions for transcribing the spoken audio stream and instructions for providing the verified document to the automatic decision support system contemporaneously.

8. The non-transitory computer-readable medium of claim 6, wherein the method further comprises:
(K) storing a record associating the decision support output with the verified document.

9. The non-transitory computer-readable medium of claim 4, wherein the method further comprises:
(K) rendering the verified document based on the decision support output to produce a rendering of the verified document.

10. The non-transitory computer-readable medium of claim 9, wherein (K) further comprises, before (F), at the automatic decision support system, labeling a first component of the decision support output with a first priority level and labeling a second component of the decision support output with a second priority level that differs from the first priority level.

* * * * *

UNITED STATES PATENT AND TRADEMARK OFFICE
CERTIFICATE OF CORRECTION

PATENT NO. : 10,339,937 B2
APPLICATION NO. : 15/892876
DATED : July 2, 2019
INVENTOR(S) : Detlef Koll Page 1 of 1

It is certified that error appears in the above-identified patent and that said Letters Patent is hereby corrected as shown below:

In the Claims

Column 12
Lines 53-54 (Approx.), In Claim 9, delete "claim 4," and insert -- claim 6, --, therefor.

Signed and Sealed this
Twenty-first Day of July, 2020

Andrei Iancu
*Director of the United States Patent and Trademark Office*